United States Patent [19]

Lévai et al.

[11] 4,259,257
[45] Mar. 31, 1981

[54] 1-PHENYL-2-AMINO-1,3-PROPANEDIOL-N-ARYLOXYALKYL DERIVATIVES

[75] Inventors: Laszló Lévai; Gabor Fazekas; Lujza Petocz; Katalin Grasser, all of Budapest, Hungary

[73] Assignee: Egyt Gyogyszervegyeszeti Gyar, Budapest, Hungary

[21] Appl. No.: 73,563

[22] Filed: Sep. 7, 1979

Related U.S. Application Data

[63] Continuation of Ser. No. 885,111, Mar. 10, 1978, abandoned.

[30] Foreign Application Priority Data

Mar. 11, 1977 [HU] Hungary .............................. EE 2484

[51] Int. Cl.³ .............................................. C07C 93/06
[52] U.S. Cl. ................................ 260/501.18; 424/316; 424/330; 564/271; 564/304; 564/316; 564/353; 564/360
[58] Field of Search ........................ 260/570.6, 501.18

[56] References Cited

U.S. PATENT DOCUMENTS 2,103,266  12/1937  Lott ............................... 260/570.6 X
3,202,711  8/1965   Fruhstorfer et al. ................. 260/570

OTHER PUBLICATIONS

Fumke et al., "Chemical Abstracts", vol. 48, p. 5141d (1954).
Cherbuliez et al., "Chemical Abstracts", vol. 25, pp. 2132–2133 (1931).

Primary Examiner—Robert V. Hines
Attorney, Agent, or Firm—Young & Thompson

[57] ABSTRACT

The invention relates to novel 1-phenyl-2-amino-1,3-propanediol-N-alkyl derivatives having the general formula I

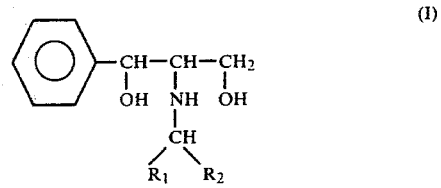

wherein $R_1$ is hydrogen, alkyl having from 1 to 8 carbon atoms or phenoxymethyl, and $R_2$ is hydrogen, alkyl having from 1 to 8 carbon atoms or 2,2-diphenylethyl, with the proviso that if $R_1$ is phenoxymethyl then $R_2$ may stand only for methyl, and if $R_2$ is 2,2-diphenylethyl then $R_1$ may stand only for hydrogen, and its isomers and pharmaceutically acceptable salts. Furthermore, the invention relates to a process for preparing these compounds.

The novel 1-phenyl-2-amino-1,3-propanediol-N-alkyl derivatives having the general formula I possess significant anti-anginose activity and show several other biological activities.

1 Claim, No Drawings

1-PHENYL-2-AMINO-1,3-PROPANEDIOL-N-ARYLOXYALKYL DERIVATIVES

This is a continuation of application Ser. No. 885,111, filed Mar. 10, 1978, and now abandoned.

This invention relates to novel compounds of antianginose activity. More particularly, the invention relates to novel 1-phenyl-2-amino-1,3-propanediol-N-alkyl derivatives having the general formula I

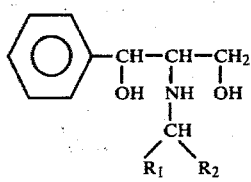

and pharmaceutically acceptable salts thereof. Furthermore, the invention relates to a process for preparing these compounds.

In the formula $R_1$ is hydrogen, alkyl having from 1 to 8 carbon atoms or phenoxymethyl; and $R_2$ is hydrogen, alkyl having from 1 to 8 carbon atoms or 2,2-diphenylethyl;

with the proviso that if $R_1$ is phenoxymethyl then $R_2$ may stand only for methyl, and if $R_2$ is 2,2-diphenylethyl then $R_1$ may stand only for hydrogen.

Pharmaceutical compositions containing these compounds as active ingredients are also within the scope of the invention.

The general formula I represents also the stereoisomers of the new propanediol-N-alkyl derivatives. It is well known that 1-phenyl-2-amino-1,3-propanediol can exist in form of threo and erythro diastereomers. Both of these forms have also optically active derivatives. The same holds in respect of the N-alkyl compounds but if the alkyl group attached to the nitrogen atom also has a centre of asymmetry compounds having three centres of asymmetry are obtained and the number of diastereomers is doubled. In this case the four racemates are designated by the terms "threo", "allothreo", "erythro", and "alloerythro", respectively.

According to the invention novel compounds having the general formula I are prepared by alkylating racemic or optically active 1-phenyl-2-amino-1,3-propanediol or the known N-benzyl derivative of same and—when the N-benzyl derivative is used—subsequently eliminating the benzyl group.

For the alkylation especially the methods where the disubstitution is negligible and thus it does not disturb the separation of the main product are advantageously used.

According to the invention compounds of the general formula I are prepared by catalytic hydrogenation of the mixture of 1-phenyl-2-amino-1,3-propanediol of the formula II

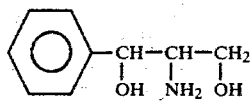

and an aldehyde or ketone of the general formula III

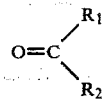

wherein $R_1$ and $R_2$ are as defined above, thus carrying out a reductive condensation.

One can proceed also by alkylating the N-benzyl derivative of 1-phenyl-2-amino-1,3-propanediol with an alkyl halide of the general formula IV

wherein $R_1$ and $R_2$ have the same meaning as defined above and Hal stands for halogen, and eliminating the benzyl group by catalytic hydrogenation of the N-benzyl-alkyl derivative obtained.

Starting compound of formula II, including stereoisomers and optically active compounds, is prepared by methods known in the art. See, for example, J.A.C.S. 2463–2468 (1949) for the preparation of racemic threo and erythro compounds; Hungarian Pat. No. 154,951 for resolving racemic mixtures. The N-benzyl derivative is also prepared by conventional means, i.e. by catalytic reduction of the corresponding benzal compound prepared by a known method (J. Org. Chem. 596/1954/), in the presence of palladium catalyst.

The compound of the general formula I obtained can be transformed, if desired, into a pharmaceutically acceptable salt by means of a mineral or organic acid.

For the reductive condensation any conventional catalysts generally used in hydrogenation reactions, i.e. Pt, Pd, Raney-Ni, Raney-Ni containing Fe etc., can be used. For laboratory purposes the use of platinic oxide proved to be especially advantageous, while on an industrial scale Raney-Ni can be most advantageously employed, under pressure. The reaction is accomplished in an alcoholic, water/alcohol or other water-miscible organic system. The pH-value of the reaction medium is preferably adjusted to mild acidic with an organic acid.

To improve the biological applicability of the instant compounds—i.e. to promote resorption—it is advisable to prepare the readily soluble salts (hydrochloride, fumarate, gluconate etc.) thereof in place of the free bases which are generally poorly soluble in aqueous media. In some instances, for example in case of the 3,3-diphenylpropyl derivatives, the gluconate salt is readily hydrolyzable due to the weak basic character and poor water-solubility of the corresponding free base, and this fact results in a cloudly solution. This undesired phenomenon would make difficulties during the preparation of solutions for injection purposes but can easily be eliminated by adding excess amount of gluconic acid and thereby repressing dissociation.

Some preferred representatives of the compounds according to the invention are set forth in the following Table 1.

TABLE 1

| Compound | Number of the compound | Example |
|---|---|---|
| L (+) threo-1-phenyl-2-isopropylamino- | | |

TABLE 1-continued

| Compound | Number of the compound | Example |
|---|---|---|
| 1,3-propanediol | 1 | 1 |
| Threo + allothreo-1-phenyl-2-phenoxy-isopropylamino-1,3-propanediol fumarate | 2 | 2 |
| (+) (Threo + allothreo)-1-phenyl-2-phenoxy-isopropylamino-1,3-propanediol fumarate | 3 | 3 |
| (−) (Threo + allothreo)-1-phenyl-2-phenoxy-isopropylamino-1,3-propanediol fumarate | 4 | |
| (Erythro+ allcerythrol)-1-phenyl-2-Erythro-1-phenyl-2-[(3',3'-diphenyl-propyl)-amino]-1,3-propanediol | 8 | 7 |

The compounds of this invention are useful for various pharmacological purposes. From the numerous biological activities exerted by them the anti-anginose activity proved to be especially important since it has been found that this activity surpasses many times the activities showed by commercial drugs known for this purpose (for example Prenilamine, i.e. 3,3-diphenylpropyl-1-methylphenethylamine). Moreover, many of the compounds are also useful as local anaesthetics and smooth muscle relaxants. There are substances which show a better activity in these fields than the known drugs—e.g. Lidocaine—conventionally used for these purposes. Due to the fact that the effective doses of the compounds according to the invention are very low and they possess an extremely low toxicity ($LD_{50}$ is often 2000 mg./kg. per os or even higher), the problems connected with toxicity can practically be neglected.

Toxicity (per os) has been determined on mice (CFLP strain) of both sexes weighing about 20 to 25 g. each, 10 mice were used for each doses and the time of observation was 96 hours. The $LD_{50}$-values calculated on the basis of the test results are listed in Table 2 below.

TABLE 2

| | Acute toxicity |
|---|---|
| Number of the compound | $LD_{50}$ (mg./kg. p.o.) |
| 1 | 710 |
| 2 | 200 |
| 3 | 350 |
| 4 | 275 |
| 5 | 2000 |

On tests carried out on cats narcotized with chloralose-urethane the novel compounds according to the invention do not show adrenolytic, ganglionparalysing and betha-receptor blocking activities and in vivo experiments proved that anti-colynergic, anti-histamine and anti-serotonin activities are also lacking. The novel compounds have no permanent effect on the blood pressure or heart frequency and are harmless on respiration.

Anti-anginose activity of the compounds according to the invention was tested on male rats from the CFY strain by the method of Nieschulz (Nieschulz, E. et al., Arzneimittelforschung, 5, 680/1955/). The rats weighed about 180 to 220 g. each and were narcotized prior to treatment. Electrocardiograms were registered by means of a NEK-2 ECG-instrument using a standard II output. The coronary insufficiency was induced with a 4 IE/kg. i.v. dose of glanduitrine. Prenilamine was used as a reference compound.

The acute intravenous toxicity was determined on rats of both sexes, using five animals for each doses. The relative anti-anginose activity was calculated on the basis of the following equation:

$$\frac{LD_{50} - \text{value mg./kg. } i.v.}{\text{Test dose mg./kg.}} \times \text{inhibition}[\%]$$

Test results are shown in Table 3 below (inhibition caused by Prenilamine = 1).

TABLE 3

| | Anti-anginose activity | | | |
|---|---|---|---|---|
| Number of the compound | $LD_{50}$-value (mg./kg., i.v.) | Test dose (mg./kg.) | Anti-anginose effect (inhibition %) | Relative efficiency |
| 1 | 140.0 | 10.0 | 50 | 3.0 |
| 2 | 11.0 | 2.0 | 56 | 1.3 |
| 3 | 21.5 | 2.0 | 67 | 3.0 |
| 5 | 45.0 | 4.0 | 64 | 3.0 |
| Prenilamine | 11.5 | 2.0 | 41 | 1.0 |
| Lidocaine | 34.0 | 4.0 | 39 | 1.4 |

The local anaesthetic activity was tested by the method of Truant and d'Amato (Truant, A. P. and Wiedling, S., Acta Chirurg. Scand. 116, 351/1958) on the N. ischiadicus of rats. The number of the animals showing the signs of characteristic motor-paralysis was recorded. As a control compound Lidocaine was used. The $LD_{50}$-values and the efficiency related to Lidocaine are given in Table 4 below. This test can be carried out with water-soluble substances only.

For the determination of smooth muscle relaxing activity the method of Brock et al. (Brock, N, et al., Arch. Exper. Pathol. u. Pharmacol., 215, 492/1952/) was used on isolated rat ileums. Papaverine was used as reference compound. In Table 4 below the $EC_{50}$-values and the relative efficiencies calculated on the basis of the following equation are also listed:

$$\text{Relative efficiency} = \frac{EC_{50} \text{ (for the control compound)}}{EC_{50} \text{ (for the test compound)}}$$

TABLE 4

| | Local anaesthetic activity | | Smooth muscle relaxant activity | |
|---|---|---|---|---|
| Number of the compound | $EC_{50}$ ($\gamma$/ml.) | Relative efficiency | $EC_{50}$ ($\gamma$/ml.) | Relative efficiency |
| 2 | 0.12 | 1.58 | 17.57 | 0.50 |
| 3 | 0.20 | 0.95 | 8.50 | 1.03 |
| 4 | 0.28 | 0.68 | 10.78 | 0.80 |
| Lidocaine | 0.19 | 1.0 | — | — |
| Papaverine | — | — | 8.78 | 1.0 |

The compounds according to the invention can be administered in a daily dose of 60 to 300 mg. in form of any usual pharmeceutical formulation.

The invention is elucidated in detail by the aid of the following non-limiting Examples.

EXAMPLE 1

L(+)-threo-1-phenyl-2-isopropylamino-1,3-propanediol hydrochloride

The solution of 8.36 g. (0.05 moles) of L(+)-threo-1-phenyl-2-amino-1,3-propanediol, 5.8 g. (0.1 moles) of acetone and 3.1 ml. of acetic acid in abs. ethanol is hydrogenated in the presence of 0.5 g. of platinic oxide pre-treated with hydrogen. Hydrogenation is allowed to continue until the calculated amount of hydrogen is used up (2400 ml. of hydrogen in about 16 hours). During the hydrogneation further three 0.2 g. portions of platinic oxide are added to the reaction mixture.

The catalyst is filtered off and the filtrate evaporated in vacuo to yield 14.7 g. of a dense oily substance. After addition of 20 ml. of ethanol and 10 ml. of a 20% solution of hydrochloric acid in ethanol (pH 3 to 4) the oily product is evaporated again in vacuo. A pale ink crystalline chlorohydrate is obtained which is then dissolved in 40 ml. of a warm 2:3 mixture of ethanol and ethyl acetate. The solution is filtered, further 20 ml. of ethyl acetate are added and the mixture is allowed to stand in a refrigerator. The precipitated crystals are filtered off.

Yield: 5.5 g. of L(+)-threo-1-phenyl-2-isopropylamino-1,3-propanediol hydrochloride melting at 162° to 165° C. When evaporating the mother liquor and treating e residue with a 2:3 mixture of ethanol and ethyl acetate further 2.85 g. of the title compound are obtained. Thus the total yield amounts to 8.35 g. (68%).

EXAMPLE 2

Threo+allothreo-1-phenyl-2-phenoxyisopropylamino-1,3-propanediol fumarate

The solution of 17.3 g. (0.103 moles) of threo-1-phenyl-2-amino-1,3-propanediol and 31.0 g. (0.206 moles) of fresh distilled phenoxyacetone in 150 ml. of ethanol is acidified with 6.2 ml. of acetic acid. The mixture is then hydrogenated in the presence of a suspension of 0.91 g. of platinic oxide in 15 ml. of ethanol, pre-treated with hydrogen. Hydrogenation is allowed to continue until the calculated amount of hydrogen is used up (4960 ml. of 20° C., in about 18 to 20 hours).

The catalyst is filtered off and the filtrate evaporated in vacuo. To the residue benzene is added and the solvent traces and acetic acid are eliminated by azeotropic distillation. The residue is dissolved in 100 ml. of abs. ethanol and the solution of 12 g. of fumaric acid in 300 ml. of ethanol is added. The solution is allowed to stand in a refrigerator overnight and the precipitated product is filtered off.

After evaporating the mother liquor to one third of its volume a further portion of the title compound is obtained. The combined products weighing 30.2 g. are recrystallized from 185 ml. of ethanol.

Total yield: 24.75 g. (57.5%) of threo+allothreo-1-phenyl-2-phenoxyisopropylamino-1,3-propanediol fumarate melting at 145° to 147° C.

EXAMPLE 3

(+)
(Threo+allorthreo)-1-phenyl-2-phenoxyisopropylamino-1,3-propanediol fumarate The solution of 13.0 g. of L(+) threo-1-phenyl-2-amino-1,3-propanediol and 23.2 g. of fresh distilled phenoxyacetone in 124 ml. of ethanol is acidified with 4.66 g. of acetic acid. The mixture is then hydrogenated in the presence of a suspension of 1 g. of platinic oxide, pre-treated with hydrogen, in 30 ml. of ethanol. Hydrogenation is allowed to continue until the calculated amount of hydrogen is used up (3720 ml. in 17 hours).

The catalyst is filtered off and the filtrate evaporated in vacuo. To the residue benzene is added, and acetic acid and the solvent traces are eliminated by azeotropic distillation.

37.1 g. of an oil substance are obtained which are then dissolved in 100 ml. of ethanol. To the solution 8.6 g. of fumaric acid in 200 ml. of ethanol are added. Evaporation in vacuo affords a yellowish oil product crystallized upon trituration with ethyl acetate. The mixture is allowed to stand in a refrigerator overnight and the product is filtered off.

Yield: 17.9 g. (55%) of (+) (threo+allothreo)-1-phenyl-2-phenoxyisopropylamino-1,3-propanediol fumarate melting at 61° to 67° C.

EXAMPLE 4

Erythro+alloerythro-1-phenyl-2-phenoxyisopropylamino-1,3-propanediol fumarate

The solution of 17.3 g. (0.103 moles) of erythro-1-phenyl-2-amino-1,3-propanediol and 31.0 g. (0.206 moles) of phenoxyacetone in 350 ml. of abs. ethanol is acidified with 6.2 ml. of acetic acid. The mixture is then hydrogenated in the presence of a suspension of 1.0 g. of platinic oxide in 30 ml. of ethanol, pre-treated with hydrogen. Hydrogenation is allowed to continue until the calculated amount of hydrogen is used up (4960 ml.).

The catalyst is filtered off and the filtrate evaporated in vacuo to yield 51.0 g. of a viscous residue. The residue is dissolved in 100 ml. of ethanol and the solution of 5.81 g. of fumaric acid in 120 ml. of ethanol having a temperature of 60° C. is added. The reaction mixture is allowed to stand in a refrigerator, filtered and dried.

Yield: 31.2 g. of the title compound melting at 170° to 179° C.

Recrystallization of the above product from 1100 ml. of ethanol affords 17.8 g. (50%) of erythro+alloerythro-1-phenyl-2-phenoxyisopropylamino-1,3-propanediol fumarate melting at 189° to 190° C.

EXAMPLE 5

Threo-1-phenyl-2-methylamino-1,3-propanediol hydrochloride

The mixture of 10.4 g. (0.04 moles) of 1-phenyl-2-benzylamino-1,3-propanediol, 7.16 g. (0.05 moles) of methyl iodide and 13.6 g. of powdered sodium carbonate is refluxed in 250 ml. of abs. acetone for 70 hours. The reaction mixture is filtered and the filtrate evaporated. Sodium iodide traces are eliminated from the residue obtained by boiling in 100 ml. of distilled water for 5 minutes. The organic phase is extracted with five 50-ml. portions of diethyl ether. The ethereal extract is dried over magnesium sulphate and the ether is distilled off to give 6.45 g. of an oily substance. After addition of petroleum ether and standing for 48 hours a crystalline precipitate is obtained which is filtered off to yield 5.35 g. of a crystalline product. The crystals are taken up in water and extracted with four 80-ml. portions of diethyl ether. Charcoal is added to the extract which is then filtered off and the ether is evaporated. Trituration of the residue with n-hexane affords threo-1-phenyl-2-benzylmethylamino-1,3-propanediol in form of white crystals.

Yield: 3.4 g. (31%); m.p. 69° to 72° C.

The above product is hydrogenated in 135 ml. of ethanol, in the presence of 0.5 g. of a Pd/C catalyst, until the calculated amount of hydrogen is used up. The catalyst is filtered off and the filtrate evaporated to yield a viscous product. The pH-value of the product is adjusted to 3 with a 20% solution of hydrochloric acid in ethanol and the mixture is evaporated to dryness. The precipitated hydrochloride salt is dissolved in 7 ml. of warm ethanol and ethyl acetate is added until the solution becomes cloudy (about 30 ml. of ethyl acetate). The mixture is allowed to stand and the crystalline hydrochloride precipitated is filtered off.

Yield: 2.72 g. (80%) of threo-1-phenyl-2-methylamino-1,3-propanediol hydrochloride melting at 125° to 127° C.

What we claim is:
1. 1-phenyl-2-phenoxyisopropylamino-1,3-propanediol and its isomers and pharmaceutically acceptable salts.

* * * * *